United States Patent [19]

Barry

[11] Patent Number: 5,603,690
[45] Date of Patent: Feb. 18, 1997

[54] INFLATABLE SUPPORTS

[75] Inventor: Thomas Barry, Cardiff, United Kingdom

[73] Assignee: South Glamorgan Health Authority, Cardiff, United Kingdom

[21] Appl. No.: 859,459
[22] PCT Filed: Nov. 29, 1990
[86] PCT No.: PCT/GB90/01861
  § 371 Date: May 29, 1992
  § 102(e) Date: May 29, 1992
[87] PCT Pub. No.: WO91/07937
  PCT Pub. Date: Jun. 13, 1991

[30] Foreign Application Priority Data

Nov. 29, 1989 [GB] United Kingdom ............ 8926920

[51] Int. Cl.$^6$ .................. A61F 5/00; A61H 7/00
[52] U.S. Cl. ............. 601/148; 601/151; 602/13
[58] Field of Search ................. 128/24 R, 64, 128/67, 845, DIG. 20; 602/13, 19; 601/148, 151

[56] References Cited

U.S. PATENT DOCUMENTS

| | | |
|---|---|---|
| 2,724,129 | 11/1955 | Pugh . |
| 3,822,425 | 7/1974 | Scales ............... 5/348 R |
| 3,824,992 | 7/1974 | Nicholson ........... 128/DIG. 20 |
| 4,185,341 | 1/1980 | Scales . |
| 4,225,989 | 10/1980 | Corbett ............... 128/33 |
| 4,280,487 | 7/1981 | Jackson ............... 128/64 |
| 4,355,632 | 10/1982 | Sandman ........... 128/24 R |
| 4,452,845 | 6/1984 | Lloyd ............... 602/52 |
| 4,628,945 | 12/1986 | Johnson ............... 602/13 |
| 5,009,318 | 3/1991 | Lepinoy ........... 128/DIG. 20 |

FOREIGN PATENT DOCUMENTS

| | | |
|---|---|---|
| 0291152 | 11/1988 | European Pat. Off. . |
| 2601874 | 1/1988 | France . |
| 8911168 | 12/1989 | Germany . |
| 1341325 | 12/1973 | United Kingdom . |
| 1355243 | 6/1974 | United Kingdom . |
| 1443759 | 7/1976 | United Kingdom . |
| 1474018 | 5/1977 | United Kingdom . |
| 1596157 | 8/1981 | United Kingdom . |
| 2141333 | 12/1984 | United Kingdom . |
| 2177595 | 1/1987 | United Kingdom . |

*Primary Examiner*—Robert A. Hafer
*Assistant Examiner*—Brian E. Hanlon
*Attorney, Agent, or Firm*—Young & Thompson

[57] ABSTRACT

An inflatable support is made of a vapour permeable material capable of sustaining an inflated state for significant periods without replenishment so as to provide good pressure distribution whilst allowing breathing to prevent sweating.

6 Claims, 2 Drawing Sheets

INFLATABLE SUPPORTS

This invention relates to an inflatable support means and, in particular but not exclusively, to an inflatable tissue support for prevention and/or repair of tissue pressure damage.

It is generally known that people who remain in static positions for long periods (e.g. the seriously injured, the brittle boned, unconscious patients, the elderly and those with certain disabilities) are particularly susceptible to pressure injuries such as decubitus ulcers or bed sores. These factors are exacerbated by the need to lie on hard surfaces such as theatre tables or firm plastic-covered mattresses.

Considerable resources in terms of nursing and extended hospitalisation are spent on the treatment of patients of all ages and conditions who develop pressure sores. According to one estimate over £2 billion is spent annually on the prevention and treatment of pressure sores. To date, most preventive measures have been expensive either in terms of increased nursing care, e.g. regular repositioning or in terms of equipment. Such equipment includes specialist units such as a net suspension bed or hammock, water beds or mattresses, air beds or cushions (both conventional and ripple-type). All this equipment is complex and expensive and the expense is difficult to justify except for those patients who have developed acute conditions. Additionally, this equipment is only partially effective.

There are many types of airbeds or cushions, and these typically are porous adjacent the patient so that air escapes from the air bed or cushion to ventilate the patient and prevent sweating. This however means that the airbed or cushion must be continually supplied with air from a blower to prevent it deflating. This is extravagant in terms of storage space, equipment cost and running costs. Another form of support consists of an array of interconnected egg-shaped inflatable cells designed to keep the patient's body immersed in the cushion. The design is costly to implement, does not allow the patient's skin to breath and is believed still to generate local pressure points.

In attempting to provide a simple and effective support for preventing a treating pressure sores which may be implemented at relatively low cost, we have unexpectedly found that it is possible to provide an inflatable support made of a material which transmits water vapour in sufficient amounts to allow a patient's skin to breathe whilst being substantially impermeable to air so that the support can stay inflated for long periods without requiring replenishment. The reason for this remarkable effect are not yet fully understood, but it is believed that it may arise because when the material is inflated and thus subjected to stress, the normal vapour permeability is inhibited thus preventing escape of the inflation medium. But the continual voluntary and involuntary movement of the user stresses and relaxes the material and thus momentarily causes local areas of the material to allow vapour to permeate.

Accordingly in one aspect this invention provides an inflatable support means formed of a breathable or vapour permeable material capable of sustaining an inflated state.

Thus, in use, the support provides the benefits of pressure distribution whilst allowing breathing of water vapour. The support may stay inflated for long periods so that it is not necessary to provide a continual source of inflation medium under pressure.

Advantageously, said material has a water vapour transmission rate in the range of from 50 to 400 g/m$^2$.d, preferably in the range of from 100–300 and ideally about 200 g/m$^2$.d.

The material is preferably a polyurethane film such as, e.g. a thermoplastic polyester urethane elastomer film.

The thickness of the material preferably lies in the range of from 25 µm to 100 µm and ideally in the range of from 50 µm to 80 µm. This provides sufficient strength whilst preserving vapour permeability.

The material is preferably made by coextrusion with a suitable carrier film. The material is preferably bonded together e.g. by heat sealing or welding to form a plurality of inflatable cells, which are advantageously interconnected to allow the inflation medium to pass therebetween.

In some applications, there may be a valve means for controlling the flow between said cells whereby the volume or pressure within a cell may be adjusted to a required level and the support means may include an inlet means for an inflation medium and means for sealing said inlet means.

The support means has many different uses, for example it may be configured for use as an interface between at least part of the body of a user and a support, or as an interface between an external support shape splint and a part of the body of a user. Furthermore the inflatable support may be used inside the body to provide support for the internal organs of a patient.

The support means may include attachment means such as adhesive tabs for allowing the support means to be secured around at least part of the body of a user.

In another aspect the invention provides a protective article for being secured around a part of a body of a user, the protective article being formed of a breathable or vapour permeable material and being configured to be spaced from a wound site or similar on the user's body and, optionally, including means for sealing or securing the article to the body.

In yet another aspect of this invention there is provided a protective article for being fitted around a part of a body of a user to prevent water reaching said body part, said protective article being formed of a breathable or vapour permeable material and, optionally, including means for sealing or securing the article to the body.

Whilst the invention has been defined above it extends to any inventive combination of the features set out above or in the following description.

The invention may be performed in various ways and certain embodiments thereof will now be described in detail, reference being made to the accompanying drawings, in which.

Figure 1:
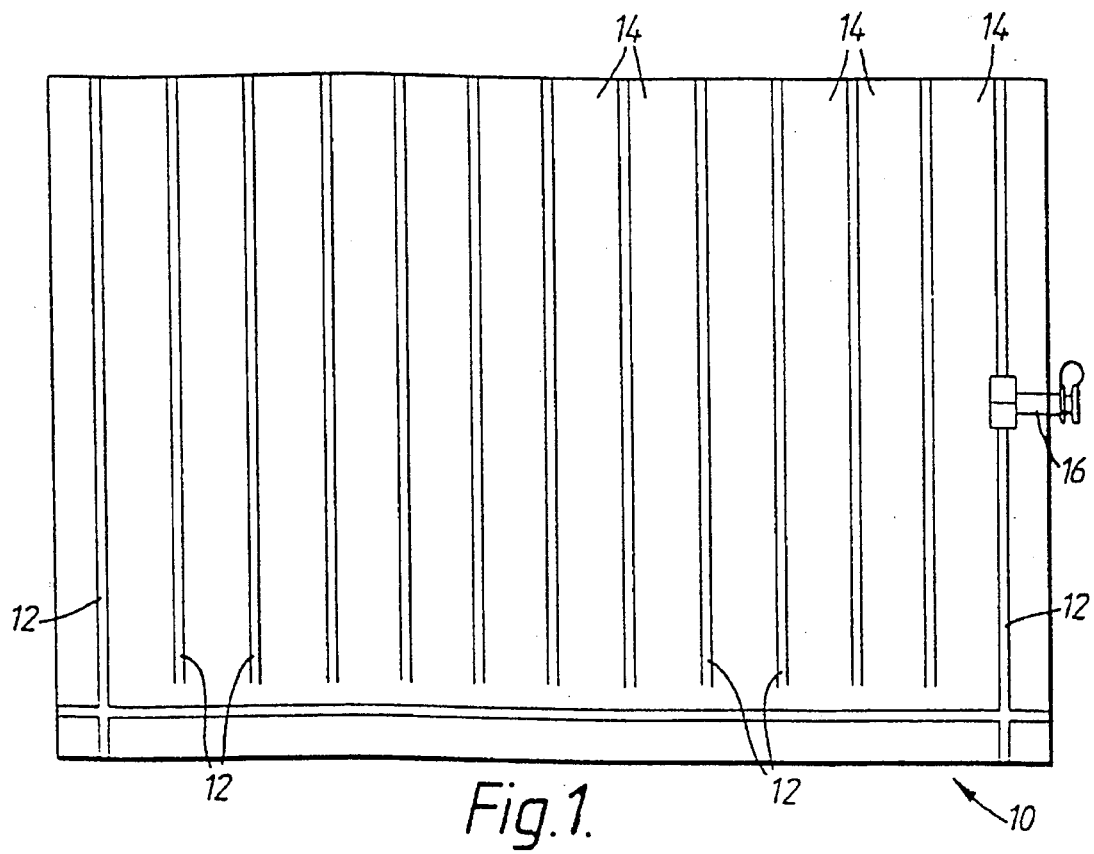
FIG. 1 is a plan view of an inflatable support interface before inflation and sealing.

Referring initially to FIG. 1, there is shown a plain inflatable interface 10 which could be located, for example beneath the buttocks of a bedbound or chairfast person. The interface comprises a sheet of extruded thermoplastic polyester urethane film folded and then heat welded along lines 12 to form a series of parallel interconnected cells 14 which inflate into a generally cylindrical shape. Instead of or in addition to heat welding, other bonding techniques may be used, for example adhesives, r.f. welding etc. The interface is inflated through an inlet 16 which is shown here as an inlet tube with a sealing stopper, but other inlet/seal arrangements may be used. For example, a "break" may be left in one of the weld lines 12 to allow inflation whereafter the break is sealed by heat welding. In the illustrated example, a single sheet of film is used to form the interface support, but if required the support may be formed from double sheets.

This type of support will normally stay sufficiently inflated for a period of months. If, however, in extreme conditions the support does deflate significantly it can be reinflated from time to time, e.g. once per nursing shift. Thus no inflation equipment is required to be permanently attached.

The inflatable interfaces may come in many different configurations depending on the particular application. For example, if an ankle cuff support is required a generally rectangular multi-celled interface of the type shown in FIG. 1 may be provided with adhesive tags so that the interface may be wrapped around the ankle and then secured in place.

Figure 2:
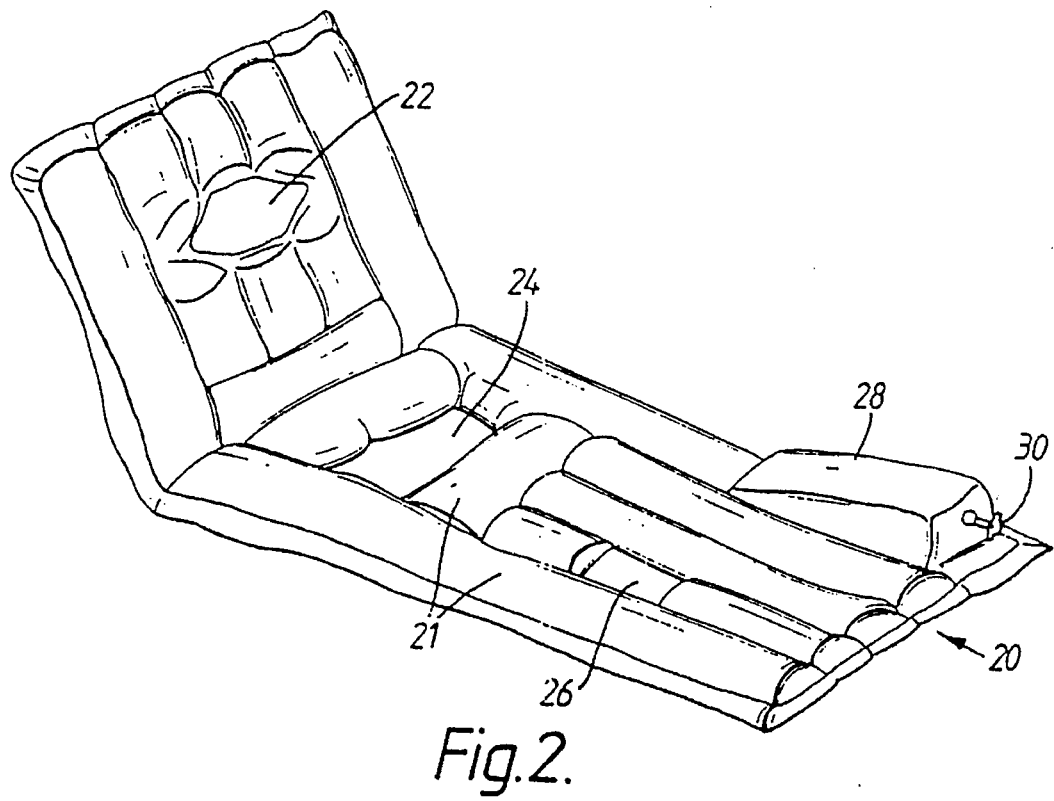
FIG. 2 is a perspective view of an inflated contoured support mattresses.

Referring to FIG. 2, the support mattress 20 formed of thermoplastic polyester urethane film to provide cells 21 in a similar manner as before. In this case however, complex geometric patterns are produced and skin contact is eliminated from specific areas e.g. at the back of the head (region 22), the buttocks (region 24) and the right calf (region 26). With this system the cells 21 may be interlinked to provide uniform hydrostatic pressure to the skin but, if required, certain cells can be isolated and include valves (not shown) to create a higher or lower pressure. The mattress of FIG. 2 also includes an elevator 28 for the left leg, and the elevator includes an inlet 30 for inflating the mattress.

Figure 3:
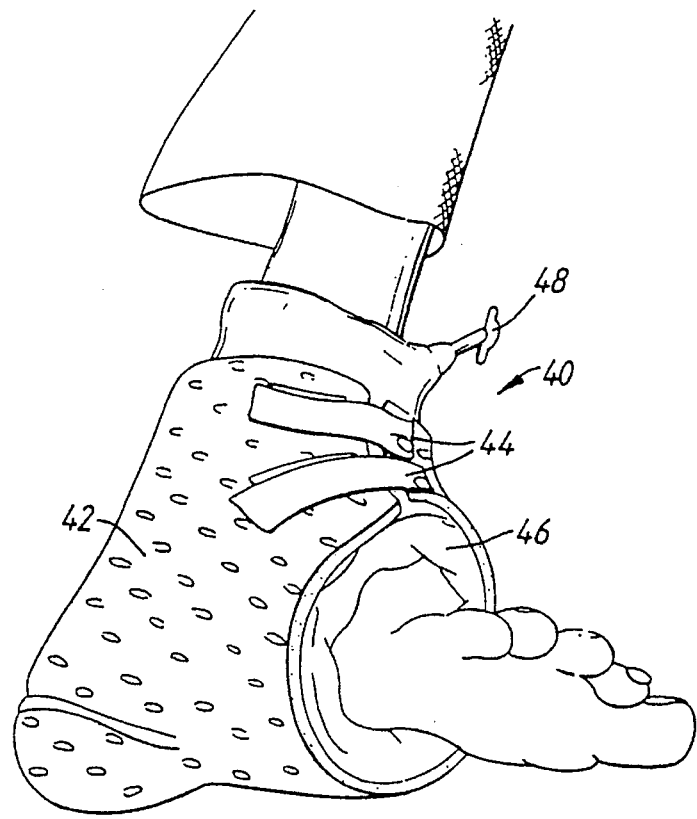
FIG. 3 shows an arrangement consisting of an outer structural splint and an inner inflated support interface.

Referring to FIG. 3 this illustrates a specialised splint 40 (e.g. to aid repair of tissue damage with an established haemophiliac) for the left ankle and foot. Firstly an outer splint 42 is constructed in a normal way using conventional materials (e.g. Plasterzote [TM]) with strapping 44 (e.g. Velcro [TM]). The outer splint 42 is made larger than normal so that a "sock" shaped cushion support 46 of thermoplastic polyester urethane film can be inserted into the splint support.

When fitted to the patient, the sock can be inflated through an inlet valve 48 to provide adequate support. The pressure in the sock 46 can be easily adjusted to provide patient comfort at all times.

Figure 4:
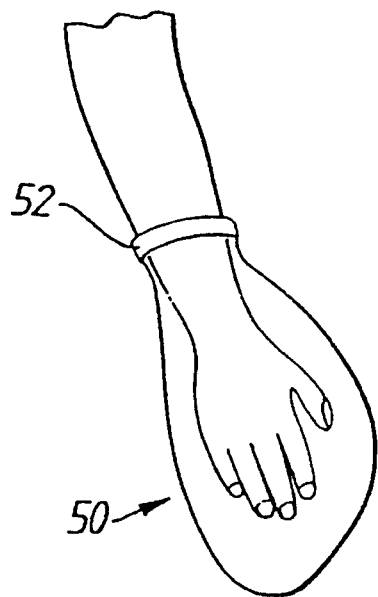
FIG. 4 shows a protective mitten.

In the embodiment of FIG. 4, a protective shield 50 for a burns patient is provided by securing a sheet of breathable thermoplastic polyester urethane film around the affected area, preferably inflating the film or otherwise minimising the possibility of the film contacting the affected area. Thus, for example, as shown an oversize mitten 50 may be provided for a patient with burns on a hand, the mitten having a cuff 52 which can be secured around an unaffected part of the wrist and preferably provided with a seal. The cuff may carry a suitable adhesive for this purpose.

Figure 5:
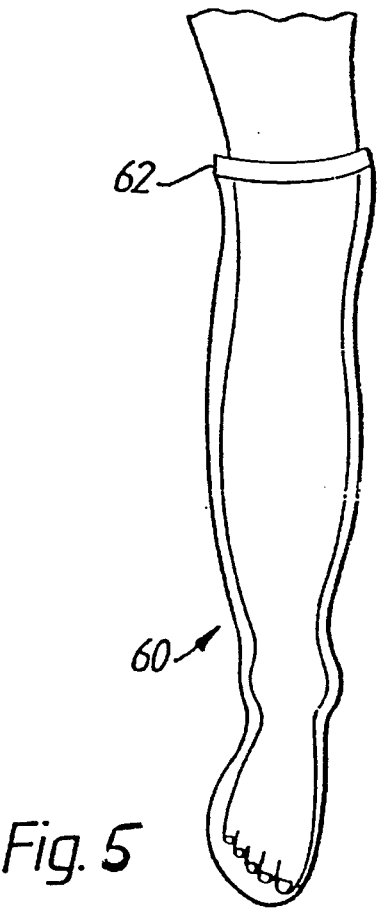
FIG. 5 shows a protective sock.

In a further embodiment shown in FIG. 5, a protective shield 60 for the leg of a patient suffering from oedema and requiring water bath treatment is shown. The shield 60 consists of a breathable thermoplastic polyester urethane film in the form of a long sock having a garter strip 62 carrying suitable adhesive for bonding it around the leg of a user. If required, the garter strip 62 may also effect sealing against the ingress of water. In use, the shield is fitted over the leg of the patient, evacuated and then bonded and sealed to the leg of the user.

In a yet further embodiment, a support may be made by filling a pouch of breathable thermoplastic polyester urethane film with polystyrene beads or other free-flowing particles, fitting the pouch around or beneath the part to be supported and then evacuating and sealing the pouch. As previously the film breathes yet is impermeable to air and so is capable of preserving the vacuum necessary to maintain its contour.

In each of the above embodiments, the breathable thermoplastic film has been a blown film extruded from thermoplastic polyester urethane elastomer which has been produced by coextrusion with a polyethylene carrier film. The elastomer film, when removed from the carrier, provides a film which we have found allows transmission of water vapour at a rate sufficient to prevent sweating, but which is substantially impermeable to air. Thus the inflated articles can sustain their inflated state for long periods which means that it is not normally necessary to re-inflate or top up the supports in use. Supports of the type shown in FIG. 1 have been used for several months without significantly deflating.

One example of a suitable material is a thermoplastic polyurethane elastomer film known as Platilon (Registered Trade Mark) UO1, manufactured and marketed by Deutsche Atochem Werke in Germany, although other materials having similar properties may be used. Two different nominal thickness have been used, 50 μm and 80 μm. The material has a segmented (i.e. alternating rigid and soft segments) and generally linear structure, and has what is termed a "slightly blocking" surface which gives it an anti-slip property. The material has a rubber-like elasticity with a low Young modulus and is capable of extreme elongation whilst having good abrasion resistance.

The water vapour transmission rate for a typical sample of material 50 μm thick is about 200 $g/m^2.d$ but suitable performance can be achieved with materials having a value in the range of from 50 to 400 and preferably from 100 to 300 $g/m^2.d$. Likewise, a typical sample of the material has a tensile strength of 55 $N/mm^2$ with an elongation of 700% at failure, and the Young modulus is below 100 MPa, preferably below 50 MPa and ideally between 2 and 10 MPa.

In addition to the breathing properties of these types of material, their elasticity qualities provide excellent pressure relief characteristics, because the material yields elastically to spread the load over a wider area when a load is applied to the inflated cell. In tests we have found that, with a typical loading, the sensed pressure applied to the patient's skin approached the theoretical minimum.

Furthermore, the anti-slip properties in combination with the elasticity mean that the surface of the interface tends to move with the skin of the user without applying a high shear to the adjacent tissue of the patient and this is believed to alleviate some of the contributory factors of pressure sores.

Moreover, the thermal conductivity of the film is sufficient to reduce the local heating that often occurs around the site of a potential pressure sore thus exacerbating the condition.

Although we mention a specific group of films other materials may be used provided they are capable of sustaining a sufficiently inflated state for, say, several hours, whilst still allowing water vapour to permeate. Other suitable materials may be selected by one skilled in the art.

I claim:

1. An inflatable support means for being inflated and sealed in use to support at least part of the body of a user, said support means including envelope means comprising a sheet of material that is permeable to water vapor but substantially impermeable to air to the extent of sustaining an inflated state by virtue of air pressure alone, said sheet having a water vapor transmission rate from 50 to 400 g/m² d, an inlet for inflation medium and means for sealing said inlet.

2. An inflatable support means according to claim 1, wherein said material has a water vapour transmission rate in the range of from 100–300 and ideally about 200 g/m².d.

3. An inflatable support means according to claim 1, wherein said material is a polyurethane film.

4. An inflatable support means according to claim 3, wherein said polyurethane film is a thermoplastic polyester urethane elastomer film.

5. An inflatable support means according to claim 1, wherein the thickness of said material lies in the range of from 25 μm to 100 μm.

6. An inflatable support means according to claim 5, wherein said thickness lies in the range of from 50 μm to 80 μm.

* * * * *